United States Patent [19]

Abrams et al.

[11] Patent Number: 5,512,305
[45] Date of Patent: Apr. 30, 1996

[54] INVITROINHIBITION OF THE HIV VIRUS WITH IONIC TUNGSTONIOBATE COMPOUNDS

[76] Inventors: Michael J. Abrams, Creek Rd., R.D. No. 2, Box 31, Glenmore, Pa. 19343; Gerald E. Bossard, 128 Spring Ridge Rd., King of Prussia, Pa. 19406; Craig L. Hill, 2941 Cravey Dr., Atlanta, Ga. 30345; Raymond F. Schinazi, 1524 Regency Walk Dr., Decatur, Ga. 30033; Brian R. C. Theobald, 15 Lea Road, Sonning Common, Reading RG4 9LH, United Kingdom

[21] Appl. No.: 66,007

[22] PCT Filed: Nov. 27, 1991

[86] PCT No.: PCT/GB91/02101

§ 371 Date: Aug. 26, 1993

§ 102(e) Date: Aug. 26, 1993

[87] PCT Pub. No.: WO92/09292

PCT Pub. Date: Jun. 11, 1992

[30] Foreign Application Priority Data

Nov. 28, 1990 [GB] United Kingdom ............... 9025847

[51] Int. Cl.⁶ .................. A61K 33/24; C01G 39/00
[52] U.S. Cl. .................. 424/617; 424/650; 423/606; 423/618; 423/593
[58] Field of Search .............. 424/617, 650, 424/606, 618, 593; 423/331, 332

[56] References Cited

U.S. PATENT DOCUMENTS

| | | | |
|---|---|---|---|
| 4,547,369 | 10/1985 | Chermann et al. | 424/131 |
| 4,634,502 | 1/1987 | Callahan et al. | 204/23 |
| 4,839,008 | 6/1989 | Hill | 204/157.15 |
| 5,051,414 | 9/1991 | Domaille et al. | 514/184 |
| 5,093,134 | 3/1992 | Murrer et al. | 424/617 |

FOREIGN PATENT DOCUMENTS

| | | |
|---|---|---|
| 0388245 | 9/1990 | European Pat. Off. |
| 0390365 | 10/1990 | European Pat. Off. |

*Primary Examiner*—Richard L. Raymond
*Assistant Examiner*—Deborah Lambkin
*Attorney, Agent, or Firm*—Oblon, Spivak, McClelland, Maier & Neustadt

[57] ABSTRACT

Tungstoniobate compounds containing an ion of general formula $$[A_x W_y Nb_a O_b]^{p-} \quad \text{I}$$

where A=P, Si, Ge, x=0 or an integer from 1 to 10, y is an integer from 1 to 10, y is an integer from 1 to 40, a is an integer from 1 to 8, b is an integer from 15 to 150, and p is an integer dependent upon the nature and oxidation state of element A, have been found to be active against viruses including especially HIV and Herpes Simplex. Pharmaceutical compositions and methods of treatment are disclosed.

6 Claims, No Drawings

INVITROINHIBITION OF THE HIV VIRUS WITH IONIC TUNGSTONIOBATE COMPOUNDS

This application is a 371 of G1391/02101 Nov. 27, 1991.

This invention concerns improvements in chemical compounds, more especially it concerns compounds and pharmaceutical compositions. In particular it concerns compositions and compounds having activity in in vitro tests on Human Immunodeficiency Virus-infected cells.

The disease known as Acquired Immune Deficiency Syndrome (AIDS) caused by infection by HIV has attracted immense research effort because of the effects of the disease on infected individuals and the dangers of the disease spreading to a wider section of the population. In general, although various chemo-therapeutic treatments have been advocated, and some compounds have emerged as a potential basis for treatment, there is still a need for alternatives. In particular, most treatments such as the compound known as AZT have a high toxicity to cells, and it would be desirable to find compounds which are less toxic. In man, the development of resistance to AZT has been identified as an additional clinical problem.

We have found certain compounds which show protective properties in in vitro screens of cells challenged with HIV-1 and/or HIV-2, and are therefore indicated as having potential for the treatment of AIDS and AIDS Related Complex and other vital and especially retroviral infections. Accordingly, the present invention provides the use of compounds defined below, in pharmaceutical compositions for treating HIV-infected patients. The invention further provides pharmaceutical compositions comprising a said compound in combination or association with a pharmaceutically acceptable diluent or excipient, for the treatment of HIV-infected patients. The invention may also be defined as the use of a said compound for the manufacture of a medicament for the treatment of HIV-infected patients. The invention further provides a process for the production of a pharmaceutical composition for the treatment of a HIV-infected patient, comprising the combination of a compound as defined below with a pharmaceutically acceptable diluent or excipient, and formulating said composition into a form suitable for administration to said patient. The invention also provides a method of treatment of an HIV-infected patient, comprising administering to said patient an effective dose of a said compound. It is to be understood that treatment includes prophylactic treatment of patients at risk, in view of the protective properties observed. Whilst this description is especially directed to combating HIV, this invention includes other aspects in which other diseases may be treated, including for example microbial infections.

It has been suggested, in JP 64-38,022, that certain salts of heteropolyacid ions of general formula $(XM_{12}O_{40})^{p-}$ where X is an ion selected from Groups III to VI or transition metal, M is one to three species selected from Mo, W, Al, V, Nb, Ta, Co and Ti, and P is a positive integer, exemplified by the two compounds $K_5BW_{12}O_{40}$ and $K_7PW_{10}Ti_2O_{40}$ which have activity against herpes virus, could be expected to have activity against human retrovirus.

It has also been reported in Chemical and Engineering News, December 1986, that silicotungstate acid, $H_4SiW_{12}O_{40}$ has activity against HIV; this compound has, however, been abandoned because of its toxicity in higher animals.

We have now discovered certain polyoxotungstoniobates of different type from those previously described, which exhibit very significant activity in conventional in vitro screening trials. Accordingly, the present invention provides as active compound, a compound selected from those containing ions of the following general formula:

$$[A_x W_y NB_a O_b]^{p-}$$

in which

A is one or more element selected from H, P, Si or Ge and x is zero or an integer from 1 to 10, y is an integer from 1 to 40, a is an integer from 1 to 8, b is an integer from 15 to 150, and p is an integer dependent upon the nature and oxidation state of element A, and their aqua complexes and active fragments.

For the purposes of the present invention, preferred ions are those in which element A is selected from one or more of H, P, Ge and Si. Preferably, when x=0, y=6-a, a is an integer from 1 to 5 and b=19; when A=Si or Ge, x=2, y=18, a=6 and b=77, and when A=P, x=2 or 4, y=12, 15, 17 or 30, a=1, 3 or 6 and b=62 or 123. The skilled man will readily appreciate that a molecule/ionic structure does not exist for every value of each integer in the above formula; examples of active structures will be given hereafter.

We believe that the above ionic structures are not necessarily maintained in solution, especially as pH changes, and it is not possible to ascertain at this time what structures are active when in contact with living cells. In particular, the structures may lose metal atoms and oxygen atoms, that is, parts of the molecule may split off yet the molecule may remain active in the antiviral tests. For example, we have identified the ion $[SiW_9Nb_3O_{40}]^{7-}$ as a potentially active fragment. Eventually, of course, if exposed to relatively high or low pH's or to other conditions which are relatively severe, degradation of the molecule will result in much simpler molecular fragments which are inactive. The invention is intended to encompass all molecular fragments of the above compounds which retain a desirable level of anti-vital activity. It is to be understood that active molecular fragments may be administered or included in pharmaceutical compositions as such, or may be made available in a number of different ways.

It is not believed that any of the above active compounds and molecular fragments have been previously proposed as having activity against retroviruses such as HIV, and the above-mentioned JP 64-38,022 does not suggest or yield in practice the active compounds and fragments of the present invention.

The active compounds of the present invention are ionic, and exist with one or more suitable counter-ions. As counter-ions may be considered especially hydrogen, alkali metal and alkaline earth metals, ammonium and ammonium substituted by one, two, three or four alkyl or aryl groups and other basic nitrogen-containing organic compounds such as amino acids. It is not believed that the counter-ion is especially critical to activity, although it may have an influence on toxicity.

The compounds may be prepared by methods as described, or analogous to methods described, in the literature. For completeness, however, preparations of several compounds are described in the following examples.

EXAMPLE 1

$(Na/K)_6[Nb_4W_2O_{19}].nH_2O$

A 200 ml solution of 10.98 g of $K_7[HNb_6O_{19}].13H_2O$ in water was added to a 200 ml solution of 33.02 g of $Na_2WO_4.2H_2O$ and 10.2 ml of 30% $H_2O_2$. The combined solution was acidified to pH 8.0 with 6M HCl (~16 ml). Acid additions were continued until the pH remained stable at 8.0.

The solution was refluxed for 10 minutes and 12.6 g of Na$_2$SO$_3$ in 50 ml of H$_2$O was added to the hot solution. The pH was readjusted to 8.0 after cooling to room temperature. After filtering the solution, cooling to 0° C. overnight gave small white crystals. The crystals were filtered off, washed with water, ethanol and ether and air dried. The yield was 10.15 g, 59% of Na$_4$K$_2$[Nb$_4$W$_2$O$_{19}$].12H$_2$O as indicated by elemental analysis and infrared spectroscopy.

EXAMPLE 2

(Me$_4$N/Na/K)$_5$[Nb$_3$W$_3$O$_{19}$].nH$_2$O

The preparation of this compound was identical to that of Nb$_4$W$_2$O$_{19}$$^{6-}$ except for being done on one-half the scale and refluxing was continued for 4 hours. After removal of Nb$_4$W$_2$O$_{19}$$^{6-}$ salts by filtration, 10 g of (Me$_4$N)Cl was added to the filtrate giving a small amount of solid. Precipitation of the product was completed by adding one volume of 95% ethanol. The white solid was filtered off, washed with water, ethanol and ether and air dried. The yield was 6.09 g, 53%, of (Me$_4$N)Na$_2$K$_2$[Nb$_3$W$_3$O$_{19}$].6H$_2$O as indicated by elemental analysis and infrared spectroscopy.

EXAMPLE 3

(Na/K/H)7[Nb$_5$WO$_{19}$].nH$_2$O

A warm solution of 18.0 g of K$_7$[HNb$_6$O$_{19}$].13H$_2$O in 200 ml of water was added to a warm solution of 32.0 g of Na$_2$WO$_4$.2H$_2$O and 18 ml of 30% H$_2$O$_2$ in 180 ml of water. The pH was lowered by dropwise addition of 1M HCl from an initial value of 11.5 until stable at 9.0. The solution was refluxed for 10 minutes then 23 g of Na$_2$SO$_3$ in 100 ml of water was added to the hot solution. The pH was adjusted to 9.0 while still warm, with 1M HCl. The solution was cooled to room temperature and filtered. Cooling to 4° C. and adding ~25 ml of ethanol gave 5.37 g of crude product. The crude product was recrystallized by dissolving 4.78 g of it in 75 ml of water, adding 10 g of KCl and cooling at 4° C. overnight. Filtering the solution and adding 15 ml of ethanol to it gave the product as a white powder, which was filtered off, washed with ethanol and ether and dried in vacuo at 25° C. The yield was 1.89 g of (Na/K/H)$_7$[Nb$_5$WO$_{19}$].H$_2$O as indicated by infrared spectroscopy.

EXAMPLE 4

(Me$_4$N)$_{15}$[HP$_4$Nb$_6$W$_{30}$O$_{123}$].16H$_2$O

A solution was made by dissolving 2.95 g of K$_7$[HNb$_6$O$_{19}$].13H$_2$O in 310 ml of water and 16.6 ml of 30% H$_2$O$_2$. Next, 29 ml of 1M HCl was added. The white precipitate was filtered off and redissolved in a minimum volume of hot water. A small amount of an insoluble material was filtered off using a fine frit and the product reprecipitated by adding 10 g of solid (Me$_4$N)Cl and cooling to room temperature. The white solid was filtered washed with a small volume of cold water and ether before drying at room temperature in vacuo. The yield was 12.77 g, 63% of (Me$_4$N)$_{15}$[HP$_4$Nb$_6$W$_{30}$O$_{123}$].16H$_2$O as indicated by elemental analysis and infrared spectroscopy.

EXAMPLE 5

(Me$_4$N)$_9$[P$_2$Nb$_3$W$_{15}$O$_{62}$].15H$_2$O.CH$_3$CN (Me$_4$N)$_{15}$[HP$_4$Nb$_6$W$_{30}$O$_{123}$].16H$_2$O, 1.45 g and (Me$_4$N)OH.5H$_2$O, 0.082 g were suspended in 35 ml of acetonitrile. A minimum volume of water was added to the stirred suspension to effect dissolution of the solids. The solution was stirred three hours, filtered and one volume of acetonitrile was added to the filtrate precipitating the white product. The solid was filtered off, washed with acetonitrile and ether and air dried. The yield was 1.20 g, 78% of (Me$_4$N)$_9$[P$_2$Nb$_3$W$_{15}$O$_{62}$].15H2O.CH$_3$CN as indicated by elemental analysis and infrared spectroscopy.

The [Nb$_3$W$_3$O$_{19}$]$^{5-}$ and [Nb$_4$W$_2$O$_{19}$]$^{6-}$ preps are essentially those found in: Dabbabi, M., Boyer, M. *J.Inorg. Nucl. Chem.*, 38, 1011–1014 (1976). The [Nb$_5$WO$_{19}$]$^{7-}$ ion is novel. The IR identification of the various M$_6$O$_{19}$ compounds is aided by the systematic shift of an absorption bond to lower energy by ~10 cm-1 on substituting each W by Nb. The band shifts from 590 cm-1 in [W$_6$O$_{19}$]$^{2-}$ to 530 cm-1 in [Nb$_6$O$_{19}$]$^{8-}$. The band for [Nb$_5$WO$_{19}$]$^{7-}$ at 540 cm-1, between those for [Nb$_4$W$_2$O$_{19}$]$^{6-}$ and [Nb$_6$O$_{19}$]$^{8-}$ at 550 and 530 cm-1, respectively.

The prep of the [P$_4$Nb$_6$W$_{30}$O$_{123}$]$^{16-}$ anion is found in: Edlund, D. J.; Saxton, R. J.; Lyon, D. K.; Finke, R. G *Organomet.*, 7, 1692–1704 (1988). It was isolated as the (Me$_4$N)$_{15}$H salt as opposed to the reported (Me$_4$N)$_{12}$H$_4$ salt. The (Me$_4$N)$_9$[P$_2$Nb$_3$W$_{15}$O$_{62}$] compound was made by a modification of a procedure found in the above reference. This material has the advantage of being stable on storage. The reported (Bu$_4$N)$_9$ salt is quoted as having, "a short shelf-life, even in the freezer compartment of a refrigerator".

EXAMPLE 6

[ME$_3$NH]$_8$[SI$_2$W$_{18}$NB$_6$O$_{77}$] Preparation modified from R. G. Finke and M. W. Droege, *JACS*, 106, 7274 (1984)

2.2 g of K$_7$H[Nb$_6$O$_{19}$] dissolved in 0.5M H$_2$O$_2$ (270 ml) was reacted with 3.6 ml of 6N HCl followed immediately by 8.93 g of A-B-Na$_9$HSiW$_9$O$_{34}$. When all of the tungsten species had dissolved NaHSO$_3$ (17.9) was slowly added to the solution, bleaching the reaction mixture from yellow to colourless. After 2 hours Me$_3$N.HCl (8.0 g) was added precipitating a white solid which was collected, washed with ethanol and ether and dried in vacuo. Yield was 6.7 g 75% (based on niobium) of [Me$_3$NH]8[Si$_2$W$_{18}$Nb$_6$O$_{77}$] as indicated by elemental analysis and infrared spectroscopy.

EXAMPLE 7

K$_7$HNbO$_{19}$.13H$_2$O (2.74, 2 mmol) was dissolved in 0.5M H$_2$O$_2$ (340 ml). 6M HCl (4,7 ml) was added to give a deep yellow solution. Solid K$_{12}$H$_2$P$_2$W$_{12}$O$_{48}$.24H$_2$O (7.88 g, 2 mmol) was then added and the solution stirred for 15 min. To destroy all the peroxides, sodium bisulphite (25 g) was carefully added to the reaction mixture. A rise in temperature was observed. This gave a colourless solution with a milky appearance. The reaction mixture was allowed to cool to room temperature and then treated with charcoal. Filtering gave a clear colourless solution which was left stirring for a further 2 h. KCl (20 g) was added and the resulting white product collected by filtration. The compound Was dissolved in water (10 ml) by warming to 40° C. and put in a refrigerator overnight. The product was collected by filtration, washed with EtOH and ether and dried in vacuo. Yield=3.91 g.

Infrared spectrum: 3425(vs,bd), 1620(s), 1088(vs), 957(s), 908(s), 780(vs), 703(bd).

| Elemental analyses (%): | | | |
|---|---|---|---|
| K | P | Nb | W |
| 4.74 | 2.17 | 18.80 | 47.16 |
| 4.70 | 2.21 | 18.49 | 46.76 |

Biological Activity

At present, there are no available animal models for HIV-1. Chimpanzees can be infected but do not develop disease. Therefore, in vitro activity towards infected cells is reported hereinbelow.

Cells. Human peripheral blood mononuclear cells (PBMC) from healthy HIV-1 seronegative and hepatitis B virus seronegative donors were isolated by Ficoll-Hypaque discontinuous gradient centrifugation at 1,000×g for 30 minutes, washed twice in phosphate-buffered saline (pH 7.2; PBS), and pelleted at 300×g for 10 minutes. Before infection, the cells were stimulated by phytohemagglutinin (FIE) at a concentration of 6 μg/ml for three days in RPMI 1640 medium supplemented with 15% heat-inactivated fetal calf serum, 1.5 mM L-glutamine, penicillin (100 U/ml), streptomycin (100 μg/ml), and 4 mM sodium bicarbonate buffer.

Viruses. HIV-1 (strain LAV-1) was obtained from Dr. P. Feorino (Centers for Disease Control, Atlanta, Ga.). The virus was propagated in human PBMC using RPMI 1640 medium, as described previously (McDougal et al, J. Immum. Meth. 76, 171–183, 1985) without PHA and supplemented with 7% v/v interleukin-2 (Advanced Biotechnologies, Silver Spring, Md.), 7 μg/ml DEAE-dextran (Pharmacia, Uppsala, Sweden), and 370 U/ml anti-human leucocyte (alpha) interferon (ICN, Lisle, Ill.). Virus obtained from cell-free culture supernatant was titrated and stored in aliquots at −80° C. until use.

Inhibition of virus replication in human

PBMC. Uninfected PHA-stimulated human PBMC were uniformly distributed among 25 cm² flasks to give a 5 ml suspension containing about 2×10⁶ cells/ml. Suitable dilutions of virus were added to infect the cultures. The mean reverse transcriptase (RT) activity of the inocula was 50,000 decompositions per min/ml corresponding to about 100 $TCID_{50}$, as determined by Groopman et al. (Groopman et al, AIDS Res. Human Retro. 3, 71–85, 1987. The drugs at twice their final concentration in 5 ml of RPMI 1640 medium, supplemented as described above, were added to the cultures. Uninfected and untreated PBMC at equivalent cell densities were grown in parallel as controls. The cultures were maintained in a humidified 5% $CO_2$-95% air incubator at 37° C. for six days after infection, at which point all cultures were sampled for supernatant reverse transcriptase (RT) activity. Previous studies had indicated that maximum RT levels were obtained at that time. The concentrations producing 50% inhibition of RT activity compared to untreated controls were measured and are reported below as $EC_{50}$ (HIV-1).

RT activity assay. Six ml supernatant from each culture was clarified from cells at 300×g for 10 minutes. Virus particles were pelleted from 5 ml samples at 40,000 rpm for 30 minutes using a Beckman 70.1 Ti rotor and suspended in 200 μl of virus disrupting buffer (50 mM Tris-Cl, pH 7.8, 800 mM NaCl, 20% glycerol, 0.5 mM phenylmethyl sulfonyl fluoride, and 0.5% Triton x-100).

The RT assay was performed in 96-well microtiter plates, as described by Spira et al. (Spira et al, J. Clin. Microbiol. 22, 97–99, 1987). The reaction mixture, which contained 50 mM Tris-Cl pH 7.8, 9mN $MgCl_2$, 5 mM dithiothreitol (DTT), 4.7 μg/ml (rA)n.(dT)$_{12-18}$, 140 μM dATP, and 0.22 μM [³H]TTP, specific activity 70.0 ci/mmel, equivalent to 17,300 cpm/pmol; NEN Research Products, Boston, Mass., was added to each well. The sample (20 μl) was added to the reaction mixture which was then incubated at 37° C. for 2 hours. The reaction was terminated by the addition of 100 μl 10% trichloroacetic acid (TCA) containing 0.45 mM sodium pyrophosphate. The acid-insoluble nucleic acids which precipitated were collected on glass filters using a Skatrom semi-automatic harvester. The filters were washed with 5% TCA and 70% ethanol, dried, and placed in scintillation vials. Four ml of scintillation fluid (Econofluor, NEN Research Products, Boston, Mass.) were added and the amount of radioactivity in each sample was determined using a Packard Tri-Carb liquid scintillation analyzer (model 2,000CA). The results were expressed in dpm/ml of original clarified supernatant.

Cytotoxicity assay. The drugs were evaluated for their potential toxic affects on uninfected PHA stimulated human PBMC. Flasks were seeded so that the final cell concentration was 2×10⁵ cells/mi. The cells were cultured with and without drug for 6 days, at which time aliquots were counted for cell viability, as assessed by the trypan blue dye-exclusion method using a hemacytometer. The median inhibitory concentration ($IC_{50}$) was calculated using the median effect method (Chou et al, Elsevier-Biosoft, Elsevier Science Publishers, Cambridge, U.K., 1985; Chou et al, Adv. Enz. Regul. 22, 27–55, 1984). The results are reported as $IC_{50}$ PBMC below.

Cell culture assays for herpes simplex.

Viruses. (HSV-1) Mycoplasma-free Vero cells, obtained from Flow Laboratory (McLean, Va.), were used for plaque assays. The methodologies for the plaque reduction [$EC_{50}$(HSV-1)] and cytotoxicity [$IC_{50}$VERO] assays have been previously described (Schinazi et al, Antimicrob. Agents Chemother. 22, 499–507, 1982), and results for several of the compounds of the invention are reported below.

The in vitro activities of compounds of the invention, as described above, are listed below:

| Compound | $EC_{50}$ (HIV-1)* | $EC_{50}$ (HSV-1)* | $IC_{50}$ PBMC* | $IC_{50}$ VERO* |
| --- | --- | --- | --- | --- |
| [Na/K]$_6$[Nb$_4$W$_2$O$_{19}$] | 0.073 | >100 | >100 | >100 |
| [Me$_4$N/Na/K]$_5$[Nb$_3$W$_3$O$_{19}$] | 8.56 | 5.66 | >100 | >100 |
| [Me$_3$NH]$_8$[Si$_2$W$_{18}$Nb$_6$O$_{77}$] | 0.081 | >1.0 | >100 | >100 |

*Conc in μM

Additional compounds considered of particular interest are:
[Me$_4$N]$_9$[P$_2$W$_{15}$Nb$_3$O$_{62}$]
[Me$_4$N]$_{15}$[HP$_4$W$_{30}$Nb$_6$O$_{123}$]
Salts of [Nb$_5$WO$_{19}$]$^{-7}$
Salts of [Ge$_2$W$_{18}$Nb$_6$O$_{77}$]$^{-8}$ The active compounds may be administered in the form of pharmaceutical compositions formulated according to well known principles and incorporating the compound, preferably in unit dose form, in combination with a pharmaceutically acceptable diluent or excipient. Such compositions may be in the form of solutions or suspensions for injection, or irrigation or be in capsule, tablet, dragee, or other solid composition or as a solution or suspension for oral administration or formulated into pessaries or suppositories or sustained release forms of any of the above or for implantation. Suitable diluents, carriers, excipients and other components are known. It may be desirable also to formulate a composition for topical administration such as an ointment or cream. The compounds of the invention may be used, in the form of a composition or alone, and possibly carried on a finely divided support, as a coating on devices which in use contact body fluids, to discourage transmission of vital infections. Examples of devices to be considered in this aspect of the invention are surgical devices and gloves and contraceptives such as condoms, and other items, appliances, wound dressings and coverings, implements etc. generally to be considered as devices according to this aspect of the invention.

The pharmaceutical compositions according to the invention may contain unit dosages determined in accordance with conventional pharmacological methods, suitably to provide active compounds in the dosage range in humans of from 0.1 to 100 mg/kg body weight per day, in a single dose or in a number of smaller doses. Preferred dosage ranges are 1 to 30 mg/kg body weight per day.

We claim:

1. A method for the in vitro inhibition of the HIV virus, comprising contacting said virus with an ionic tungstoniobate compound selected from those containing ions of formula (I)

$$[A_x W_y Nb_a O_b]^{p-} \qquad I$$

wherein

A is one or more element selected from the group consisting of H, P, Si and Ge;

x is zero or an integer from 1 to 10;

y is an integer from 1 to 40;

a is an integer from 1 to 8;

b is an integer from 15 to 150; and p is an integer dependent upon the nature and oxidation state of element A, and their aqua complexes and active fragments.

2. The method of claim 1, wherein in the ion of formula I, A is selected from one or more of H, P, Ge and Si.

3. The method of claim 1, wherein in the ion of formula I, x=0, y=6-a, a is an integer from 1 to 5 and b=19.

4. The method of claim 1, wherein in the ion of formula I, A=Si or Ge, x=2, y=18, a=6 and b=77.

5. The method of claim 1, wherein in the ion of formula I, A=P, x=2 or 4, y=12, 15, 17 or 30, a=1, 3 or 6 and b=62 or 123.

6. The method of one of the preceding claims, wherein said tungstoniobate compound has as counter-ions, hydrogen, alkali metal, alkaline earth metal, ammonium substituted ammonium or another basic nitrogen-containing organic compound.

* * * * *

UNITED STATES PATENT AND TRADEMARK OFFICE
CERTIFICATE OF CORRECTION

PATENT NO. : 5,512,305
DATED : April 30, 1996
INVENTOR(S) : Michael J. ABRAMS, et al.

It is certified that error appears in the above-indentified patent and that said Letters Patent is hereby corrected as shown below:

On title page, item [54], & Column 1, the title, should read:

--IN VITRO INHIBITION OF THE HIV VIRUS
WITH IONIC TUNGSTONIOBATE COMPOUNDS--

Signed and Sealed this

Twentieth Day of August, 1996

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,512,305
DATED : April 30, 1996
INVENTOR(S) : Michael J. ABRAMS et al Page 1 of 4

It is certified that error appears in the above-indentified patent and that said Letters Patent is hereby corrected as shown below:

In the title page, item [57], ABSTRACT, lines 7 and 8, delete, "y is an integer from 1 to 10,".

Column 2, line 1, "$[A_x W_y NB_a O_b]^{p-}$"; should read

--$[A_x W_y Nb_a O_b]^{p-}$--;

line 35, "anti-vital", should read --anti-viral--;

line 56, delete comma after "methods described".

UNITED STATES PATENT AND TRADEMARK OFFICE
CERTIFICATE OF CORRECTION

PATENT NO. : 5,512,305
DATED: : April 30, 1996
INVENTOR(S) : Michael J. ABRAMS et al It is certified that error appears in the above-identified patent and that said Letters patent is hereby corrected as shown below:

Column 3, line 25, "(Na/K/H)7Nb$_5$WO$_{19}$].nH$_2$O" should read

--(Na/K/H)$_7$Nb$_5$WO$_{19}$].nH$_2$O--;

line 54, insert a comma after "filtered";

line 62, "(Me$_4$N)$_{15}$[HP$_4$Nb$_6$W$_{30}$O$_{123}$].16H$_2$O, 1.45 g and (Me$_4$N)OH.5H$_2$O, 0.082 g" should read --(Me$_4$N)$_{15}$[HP$_4$Nb$_6$W$_{30}$O$_{123}$].16H$_2$O (1.45 g) and (Me$_4$N)OH.5H$_2$O (0.082 g)--.

Column 4, line 3, "(Me$_4$N)$_9$[P$_2$Nb$_3$W$_{15}$O$_{62}$].15H2O.CH$_3$CN" should read --(Me$_4$N)$_9$[P$_2$Nb$_3$W$_{15}$O$_{62}$].15H$_2$O.CH$_3$CN--;

line 10, "~10 cm-1" should read --~10 cm$^{-1}$--;

line 11, "590 cm-1" should read --590 cm$^{-1}$--;

line 11, "530 cm-1" should read --530 cm$^{-1}$--;

line 12, "540 cm-1" should read --540 cm$^{-1}$--;

line 14, "530 cm-1" should read --530 cm$^{-1}$--;

UNITED STATES PATENT AND TRADEMARK OFFICE
CERTIFICATE OF CORRECTION

PATENT NO. : 5,512,305
DATED : April 30, 1996
INVENTOR(S) : Michael J. ABRAMS et al It is certified that error appears in the above-identified patent and that said Letters patent is hereby corrected as shown below:

line 27, "$[ME_3NH]_8[SI_2W_{18}NB_6O_{77}]$" should read

--$[Me_3NH]_8[Si_2W_{18}Nb_6O_{77}]$--;

line 37, "$[Me_3NH]8[Si_2W_{18}Nb_6O_{77}]$" should read

--$[Me_3NH]_8[Si_2W_{18}Nb_6O_{77}]$--;

line 52, "Was dissolved" should read

--was dissolved--.

Column 5, line 27, "PBMC" should read

--Peripheral Blood Mononuclear Cells.--;

line 35, insert a parenthesis after 1987.--.

UNITED STATES PATENT AND TRADEMARK OFFICE
CERTIFICATE OF CORRECTION

PATENT NO.   :   5,512,305
DATED:       :   April 30, 1996
INVENTOR(S)  :   Michael J. ABRAMS et al It is certified that error appears in the above-identified patent and that said Letters patent is hereby corrected as shown below:

Column 6, line 54, "$[Nb_5WO_{19}]^{-7}$" should read --$[Nb_5WO_{19}]^{7-}$--;

line 55, "$[Ge_2W_{18}Nb_6O_{77}]^{-8}$" should read --$[Ge_2W_{18}Nb_6O_{77}]^{8-}$--.

Column 8, line 23, insert a comma after "ammonium".

Signed and Sealed this

Fourth Day of August, 1998

Attest:

BRUCE LEHMAN

Attesting Officer

Commissioner of Patents and Trademarks